United States Patent
Yoshino et al.

(10) Patent No.: US 7,582,799 B2
(45) Date of Patent: Sep. 1, 2009

(54) METHOD FOR PRODUCING HYDRAZONE DERIVATIVES

(75) Inventors: Hiroshi Yoshino, Narashino (JP); Kentaro Kobayashi, Narashino (JP); Yuichi Shiro, Chiba (JP)

(73) Assignees: Shiratori Pharmaceutical Co., Ltd., Narashino-shi (JP); Asubio Pharma Co., Ltd., Tokyo (JP)

( * ) Notice: Subject to any disclaimer, the term of this patent is extended or adjusted under 35 U.S.C. 154(b) by 97 days.

(21) Appl. No.: 11/911,441

(22) PCT Filed: Apr. 27, 2006

(86) PCT No.: PCT/JP2006/309204

§ 371 (c)(1), (2), (4) Date: Oct. 12, 2007

(87) PCT Pub. No.: WO2006/118322

PCT Pub. Date: Sep. 11, 2006

(65) Prior Publication Data

US 2009/0076305 A1      Mar. 19, 2009

(30) Foreign Application Priority Data

Apr. 28, 2005   (JP) .............................. 2005-133148

(51) Int. Cl.
C07C 315/02   (2006.01)
C07C 45/41    (2006.01)
C07C 45/54    (2006.01)
C07C 241/00   (2006.01)

(52) U.S. Cl. ........................... 568/32; 568/28; 568/486; 568/496; 564/250

(58) Field of Classification Search ....................... None
See application file for complete search history.

(56) References Cited

FOREIGN PATENT DOCUMENTS

WO      94 21603      9/1994

OTHER PUBLICATIONS

Database CAPLUS on STN, Acc. No. 1954:56481, Macdonald et al., Biochimica et Biophysica Acta (1953), 12, p. 203-206 (abstract).*
Database CASREACT on STN, No. 48:56481, Macdonald et al., Biochimica et Biophysica Acta (1953), 12, p. 203-206 (reaction).*
Database CAPLUS on STN, Acc. No. 1956:15997, Zinner et al., Chemische Berichte (1955), 88, p. 566-572 (abstract).*
Database CASREACT on STN, No. 50:15997, Zinner et al., Chemische Berichte (1955), 88, p. 566-572 (reaction).*
Armarego, et al., "Pterins. VIII The Absolute Configuration at C 6 of Natural 2-Amino-6-[(1'R,2' S)-1',2'-dihydroxyprophyl]-5,6,7,8-tetrahydropteridin-4(3H)-one (L-erythro-5,6,7,8-Tetrahydrobiopterin)", Australian Journal of Chemistry, vol. 93, No. 4, pp. 785-794, XP009063789, 1982.

* cited by examiner

*Primary Examiner*—Brian J Davis
(74) *Attorney, Agent, or Firm*—Oblon, Spivak, McClelland, Maier & Neustadt, P.C.

(57) ABSTRACT

The present invention provides an industrially advantageous process for producing hydrazone derivative represented by the formula (5), which is shown by the following reaction formula.

4 Claims, No Drawings

METHOD FOR PRODUCING HYDRAZONE DERIVATIVES

TECHNICAL FIELD

The present invention relates to a process for producing a hydrazone derivative which is one of the important intermediate for the manufacture of sapropterin hydrochloride and like drug medicines.

BACKGROUND ART

Sapropterin hydrochloride (L-tetrahydrobiopterin dihydrochloride) is widely used as a therapeutic agent for atypical hyperphenylalaninemia. Sapropterin hydrochloride is produced by first producing a hydrazone derivative from L-rhamnose through L-rhamnose diethyl mercaptal (REM) and 5-deoxy-L-arabinose (5-DA), then acetylating the resultant hydrazone derivative and reacting the acetylated hydrazone derivative with 6-hydroxy-2,4,5-triaminopyrimidine, eliminating acetyl groups therefrom, and subsequently subjecting the thus deacetylated product to asymmetric reduction (cf. patent literature 1 and nonpatent literature 1).

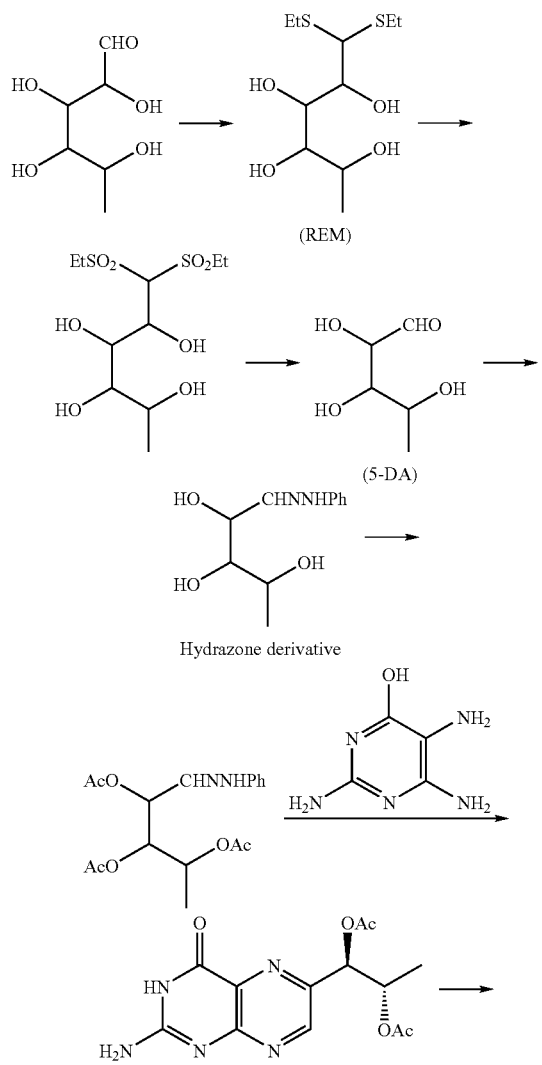

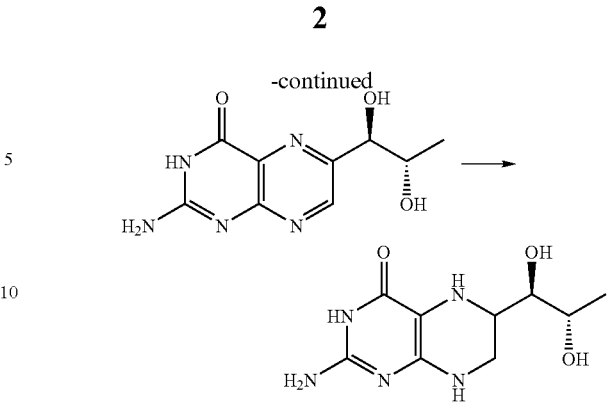

As described above, the hydrazone derivative is an important intermediate in the production process of sapropterin hydrochloride. However, this method has so far been disadvantageously affected by the difficulties that the steps covering from the L-rhamnose diethyl mercaptal (REM) to 5-DA above in the production process of hydrazone derivative involve a very low reaction yield and a very inferior reproducibility along with a long reaction time and complicated postprocessing.

[Patent literature 1] Japanese published unexamined patent application JP A S59-186986
[Nonpatent literature 1] Helv. Chim. Acta 68(6)1639-1643 (1985)
[Patent literature 2] U.S. Pat. No. 3,505,329
[Nonpatent literature 2] J. Am. Chem. Soc. 96. 6781 (1974)

DISCLOSURE OF THE INVENTION

Problems to be Solved by the Invention

Accordingly, an object of the present invention is to provide an industrially advantageous process for producing a hydrazone derivative which is an important intermediate for the production of sapropterin hydrochloride, as described previously.

Means to Solve the Problems

In the course of studying from various aspects what causes the reduction in the yield of hydrazone derivative, the inventors have found that it is attributable to the oxidation process of REM. Specifically, to oxidize REM on an industrial scale, hydrogen peroxide, perbenzoic acid, peracetic acid or like agents are used as oxidants (cf. patent literature 2 and nonpatent literature 2), it has been revealed that when such oxidizing agents are used, the reaction inevitably accompanies side reactions such as the decomposition of the reaction product and the generation of dehydration products as the reaction proceeds, thus substantially interfering with the improvement of the reaction yield. Further, it has been proved that such side reactions occurring this way act to reduce the yields in the reaction from the oxidized intermediates to 5-DA and in the hydrazonation reaction and also to lower the purity of the resultant hydrazone derivative. Moreover, the prior art method has a problem of low working efficiency or productivity in that the process undergoes intense heat generation when dripping or charging the above-described conventional oxidizing agents and thus there is involved a problem of low working efficiency with extended working hours. For the postprocessing method, using the conventional oxidizing agents also has a number of problems of requiring complicated and multistep processes, including the time required for adding a reducing agent and a step of concentrating the solvent.

Under these circumstances, the inventors have found that, when a monopersulfate is used as an oxidizing agent of the REM, substantially any such side reactions as observed in the prior art method do not occur unexpectedly with the reaction solution maintained very cleanly, and the formation of 5-DA and the hydrazonation reaction also proceed as quantitatively expected, and have accomplished the present invention.

Accordingly, the present invention provides a process for producing a 1,1-bis-alkylsulfonyl compound represented by the general formula (2)

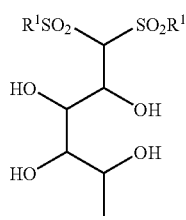
(2)

(where $R^1$ represents an alkyl group)

comprising:

reacting a 1,1-bis-alkylsulfanyl compound represented by the general formula (1):

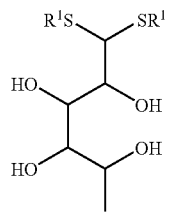
(1)

(where, $R^1$ is the same as defined above)

with a monopersulfate to produce a 1,1-bis-alkylsulfonyl compound represented by the general formula (2) above.

Also, the present invention provides a process for producing an aldehyde compound represented by the general formula (3)

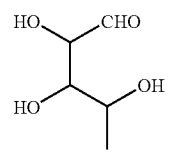
(3)

comprising:
reacting a 1,1-bis-alkylsulfanyl compound represented by the general formula (1)

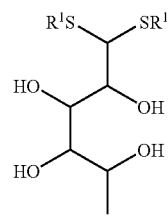
(1)

(wherein $R^1$ represents an alkyl group)

with a monopersulfate to produce a 1,1-bis-alkylsulfonyl compound represented by the general formula (2)

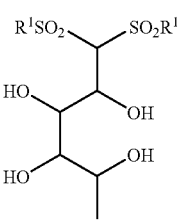
(2)

(wherein $R^1$ is the same as defined above)

and reacting the resultant 1,1-bis-alkylsulfonyl compound (2) with ammonia.

Further, the present invention provides a process for producing hydrazone derivative represented by the general formula (5),

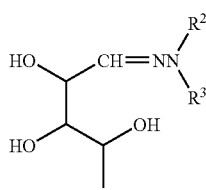
(5)

(wherein $R^2$ and $R^3$, which may be the same or different from each other, each represents an hydrogen atom, an alkyl group, or aryl group)

comprising:
reacting a 1,1-bis-alkylsulfanyl compound represented by the general formula (1)

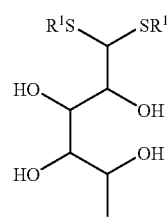
(1)

(wherein $R^1$ represents an alkyl group)

with a monopersulfate to produce a 1,1-bis-alkylsulfonyl compound represented by the general formula (2)

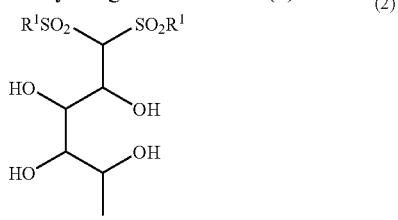

(2)

(wherein $R^1$ is the same as defined above), and reacting the resultant 1,1-bis-alkylsulfonyl compound (2) with ammonium to produce an aldehyde compound represented by the general formula (3):

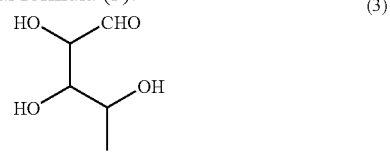

(3)

and reacting with the resultant aldehyde compound (3) with a hydrazine compound represented by the general formula (4):

(4)

(wherein $R^2$ and $R^3$ are the same as defined above.)

Advantageous Effects of the Invention

According to the method of the present invention, the oxidation reaction of the thioethers proceeds quickly to complete in a very short time with a high yield, the reaction control can be readily accomplished due to substantial nonoccurence of any side reactions, and all three process steps leading up to the hydrazone derivative proceed as substantially quantitatively expected. Further, since all the reactions from the thioethers to the hydrazone derivative do not undergo side reactions, all the three process steps involved may be performed in one-pot operation.

BEST MODE FOR CARRYING OUT THE INVENTION

The method of the present invention may be represented by the following reaction formula:

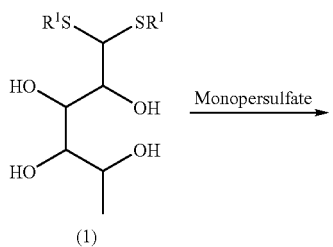

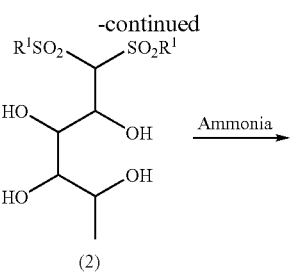

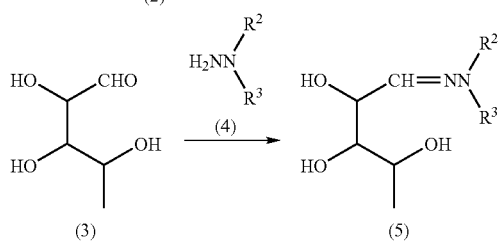

(where, $R^1$, $R^2$ and $R^3$ are the same as defined above.)

The 1,1-bis-alkylsulfanyl compound (1) which is the starting material for the present invention may be produced, for example, by adding 2 molar equivalents of ethanethiol to L-rhamnose in an aqueous solution of hydrochloric acid under ice cooling so as to react the ethanethiol with the L-rhamnose over a 20 hours period of time still under ice cooling, then filtering the resultant solution to separate out the deposited crystals therefrom, washing the resultant crystals with iced water and n-hexane, and drying the washed crystals. Here, the alkyl group represented by $R^1$ includes linear or branched alkyl groups having a 1 to 8 carbon atoms, such as methyl group, ethyl group, n-propyl group, isopropyl group, n-butyl group, or etc., and preferable examples of $R^1$ include alkyl groups having 1 to 5 carbon atoms and particularly preferably ethyl group.

The compound (2) is produced by reacting the compound (1) with a monopersulfate. As the monopersulfate, alkali metal monopersulfates may be used, including potassium monopersulfate ($KHSO_5$), sodium monopersulfate ($NaHSO_5$), and etc. The monopersulfate may be in the form of a mixture such as one having a $2 KHSO_5 \cdot KHSO_4 \cdot K_2SO_4$ formulation commercially available under the tradename "OXONE" from DuPont. When using OXONE® as the monopersulfate, the OXONE® ($=2KHSO_5 \cdot KHSO_4 \cdot K_2SO_4$) may be added preferably 2 to 3.5 molar equivalents to the compound (1), more preferably 2 to 3 molar equivalents and particularly preferably 2.2-2.4 molar equivalents.

For the reaction solvent according to the present invention, it is preferable to use water or lower alcohols and above all water is preferred. Here, such preferable lower alcohols include those alcohols having 1 to 5 carbon atoms, such as methanol, ethanol, isopropanol, or etc. The reaction solvent may be used preferably 10 to 30 times and particularly preferably 10 to 20 times the volume of the compound (1). Besides, the reaction temperature may range preferably from 5° C. to 20° C. and more preferably from 5° C. to 15° C., and particularly preferably 5° C. to 10° C. in order to prevent any side reactions from occurring. Meanwhile, the reaction time may range preferably from 1 to 10 hours, more preferably from 1 to 5 hours and particularly preferably from 2 to 5 hours in order to prevent any side reactions and to fully complete the reaction.

The compound (3) is produced by reacting the compound (2) in the resultant solution above with ammonia. This reaction may be carried out just as a continued process from the preceding step producing the compound (2) from the compound (1).

Here, the ammonia may be provided in the form of a 14 to 28% ammonia water. This reaction is carried out preferably at pH8 or above, preferably at pH8 to pH10 and particularly preferably at pH9 to pH10. Also, it is preferred that the reaction be carried out at 5° C. to 35° C. over 1 to 50 hours period of time and particularly over 10 to 40 hours.

Upon completing the reaction, the compound (3) can be readily obtained with a high purity merely by washing the reaction product with ethyl acetate, toluene, chloroform or a like organic solvent.

The compound (5) (hydrazone derivative) is produced by reacting the compound (3) with the compound (4).

The alkyl groups represented by $R^2$ and $R^3$ in the above formula (4) may include linear or branched lower alkyl groups having 1 to 7 carbon atoms such as, for example, methyl group and ethyl group, of which the methyl group is preferred. The aryl groups represented by $R^2$ and $R^3$ may include those aryl groups having 6 to 14 carbon atoms such as, for example, phenyl group and naphthyl group, among which the phenyl group is preferred. Hydrogen atom or phenyl group is particularly preferred for the atom groups represented by $R^2$ and $R^3$. The hydrazine compounds (4) used for this process step may include, for example, hydrazine, 1,1-dimethyldiazine and phenylhydrazine, among which the phenylhydrazine is particularly preferred.

This reaction may be carried out in a solvent such as water, alcohol, or etc., among which water is particularly preferred. The hydrazine compounds (4) may be added preferably 1 to 1.5 molar equivalents to the compound (3) and particularly preferably 1 to 1.1 molar equivalents. The reaction of this step may be carried out under acidic condition preferably at about pH4.0 to about pH6.5. Acids added to the reaction solution in this step may include organic acids such as acetic acid and inorganic acids such as hydrochloric acid and sulfuric acid.

It is preferred that the reaction be carried out at about 0° C. to 50° C. over 1 to 20 hours period of time. Upon completion of the reaction, the compound (5) can be readily obtained with a high purity by extracting the aqueous layer of the reaction solution with an organic solvent.

According to the method of the present invention, all the process steps producing the compound (5) from the compound (1) may be performed in a single solvent, particularly in an aqueous solution. Moreover, all of the process steps, especially the oxidation reaction, requires only a short reaction time without necessity of any postprocessing steps, thus providing industrially advantageous features. The present invention provides an industrially advantageous manufacturing method in that the process steps producing the compound (5) from the compound (1) are substantially free from any side effects and thus can dispense with any column operations or concentration operations as used in the prior art.

The resultant hydrazone derivative (5) produced above may be used for the production process of sapropterin hydrochloride known in the art as herein described previously.

EXAMPLES

Hereinafter, the present invention will be described in further detail with reference to examples thereof, but the present invention is not in any manner limited to such specific examples.

Example 1

1. 1,1-bis-ethylsulfanylhexane-2,3,4,5-tetraol (REM) (200.00 g, 0.7396 mol) and water (3,000 ml) were placed in a 5,000 ml 4-neck reaction flask to be suspended therein and then cooled down to an external temperature of 5° C. To this reaction solution, were added OXONE® (produced by DuPont; 1,046 g, 1.701 mol) while keeping an internal temperature at 20° C. or below. After the OXONE® introduction, the mixture was stirred at 5° C. for 2 hours and the reaction endpoint was determined using thin-layer chromatography (TLC) (compound (1): Rf=0.7, compound (2): Rf=0.45, TLC conditions; plate: silica gel for thin layer chromatograph, spot volume: 2 µl, developing solvent: chloroform/methanol/acetic acid (10:2:1), developed length: 5-10 cm, coloring reagent: (1:1) mixture of 1% aqueous solution of cerium (IV) sulfate/10% sulfuric acid, operational procedure: The TLC plate having undergone the development under the above-described conditions were sprayed uniformly with the coloring reagent and heated.) A 28% ammonia water was dripped into the suspended reaction solution while keeping the flask internal temperature at 25° C. or below so as to adjust the reaction solution to pH9-pH10. After stirring the suspended reaction solution at an external temperature of 10° C. over 15.5 hours period of time from the termination of the ammonia water dripping, the reaction endpoint was determined by TLC (under the same conditions as above, compound (3): Rf=0.3). Then, after filtering the reaction solution, the filtration residue was successively knead-washed first with ethyl acetate (1000 ml) and then water (200 ml), and the residue was checked by TLC (under the same conditions as above) to see if the target product (2,3,4-trihydroxypentanal) remains there. After separating the filtrate and washing the aqueous layer twice with ethyl acetate (1000 ml), the organic layer was mixed therewith and then water (200 ml) was added thereto and the resultant mixture was subjected to extraction again. Then, the aqueous layer was mixed therewith to obtain an aqueous solution (4,485 g) containing 2,3,4-trihydroxypentanal (5-DA).

2. The aqueous solution (897 g) prepared in the preceding process steps above containing 5-DA was introduced into the 2,000 ml 4-neck flask and the resultant reaction solution was cooled to an external temperature of 10° C. in an argon stream. Acetic acid (4.20 g) was added to the reaction solution to adjust it to pH5 to pH6, and subsequently phenylhydrazine (16.00 g, 0.148 mol) was added thereto. After stirring the reaction solution at a flask external temperature of 10° C. for 1 hour, the reaction endpoint was determined by TLC (under the same TLC conditions as in the example 1 above; compound (5): Rf=0.56). A 20% aqueous solution of sodium hydroxide (4.05 g) was added to the reaction solution so that the pH value of the orange-colored suspended reaction solution came to around 7, and then ethyl acetate (200 ml) and sodium chloride (225 g) were added. After separating the reaction solution, ethyl acetate (200 ml) was added to the aqueous layer and the resultant reaction solution was subjected to extraction again. Then, the organic layer was mixed therewith and anhydrous sodium sulfate (40 g) was added thereto, and the resultant mixture was dehydrated and filtered to obtain an ethyl acetate solution (500 ml) containing phenylhydrazone derivative(5).

A quantitative analysis of the ethyl acetate solution and the separated aqueous layer for the resultant phenylhydrazone derivative contained therein revealed a 102.4% yield in the ethyl acetate solution and a 0.58% yield in the aqueous layer, respectively, based on the phenylhydrazone derivative content.

The HPLC (high-performance liquid chromatography) conditions; column: Inertsil ODS-2, 4.6 mm×250 mm, column temperature: 40° C., mobile phase: 10 mM $KH_2PO_4$ (pH3-pH3.3)/acetonitrile=7:3, flow rate: 1.0 ml/min., measurement wavelength: 247 nm, analysis time: 30 minutes, internal standard: nitrobenzene, operational procedure: 1 ml reaction solution was taken and methanol was added thereto until the 20 ml marked line is reached. 5 µl of the resultant solution was injected into the column for analysis.

Example 2

1 g REM was suspended in 15 ml water and stirred at an external temperature of 5° C., and then OXONE® of 2.1 to 2.4 molar equivalents was added thereto and the resultant reaction was tracked using TLC (under the same TLC conditions as in the example 1 above). As a result, the oxidation reaction was fully completed in 2 to 5 hours. Moreover, this reaction did not undergo generation of spots of the side reaction products as observed in the comparative examples 1 through 3, to be described herein later, in which other peracids were used.

Example 3

1 g REM was suspended in 15 ml water and OXONE® of 2.3 molar equivalents was added to the suspension with the reaction temperature set at 5° C. to 10° C., and the resultant reaction was tracked using TLC (under the same TLC conditions as in the example 1 above). As a result, the oxidation reaction was fully completed at 5° C. to 10° C. in 2 to 5 hours without hardly undergoing any side reactions.

Example 4

100 g REM was dissolved in 1.5 l methanol and OXONE® of 3 molar equivalents was added to the solution at an external temperature of 20° C., and the resultant reaction was tracked using TLC (under the same TLC conditions as in the example 1 above). Sixteen hours later therefrom, the oxidation reaction was completed without hardly undergoing any side reactions.

Comparative Example 1 (Hydrogen Peroxide Method)

8.25 l acetic acid was added to 1.5 Kg REM and stirred at a 15° C. external temperature and 1,185.64 g of 35% hydrogen peroxide solution was dripped there at an internal temperature of 30° C. or below over about 8 hours period of time. After stirring the reaction solution all night, 18.04 g concentrated hydrochloric acid was added thereto and the resultant reactant solution was warmed to 40° C. external temperature, and then 1778.39 g of 35% hydrogen peroxide solution was again dripped into the reaction solution over about 30 minutes period of time. After stirring the resultant reaction solution at a 40° C. external temperature over about 9 hours period of time, it was cooled at a 10° C. external temperature, and 750 ml of an aqueous solution containing 60.02 g dissolved sodium acetate was added to the reaction solution, which was then stirred all night. The resultant reaction solution was cooled at a 0° C. external temperature and 3 l of an aqueous solution containing 525.27 g dissolved sodium hydrosulfite was dripped until the oxidation-reduction potential reached 436 mV, and the resultant solution was stirred all night at 5° C. external temperature. The reaction solution was subjected to vacuum concentration at a 60° C. external temperature until the internal temperature stopped rising. The concentration residue was used for the next process step. Several spots of the side reaction products were observed in a thin-layer chromatography (TLC) of the concentration residue (under the same TLC conditions as in the example 1 above). Thereafter, the reaction solution was subjected to an ammoniation step and then a phenylhydrazonation step, like the example 1. This resulted in an yield of 45% to 75% of the hydrazone derivative.

Comparative Example 2 (Peracetic Acid Method)

3.55 g of 32% peracetic acid (diluted acetic acid solution) and 1 ml water were introduced into a flask and stirred at a 10° C. external temperature, and 1 g REM was added dividedly to the reaction solution. The reaction solution was stirred all night at a 30° C. external temperature and 21 hours later a reaction endpoint was determined using TLC (under the same TLC condition as in the example 1 above). The reaction solution was ice-cooled and 0.35 g of sodium hydrosulfite was added slowly thereto, and upon determining a disappearance of peroxides in the reaction solution with a potassium iodide starch test paper the reaction solution was subjected to vacuum concentration at 50° C. external temperature. A 2.337 g mixture of a white solid and an oily matter was obtained as the concentration residue. A TLC of the concentration residue revealed that the reaction product mainly comprised a dehydrated product (6,6-bis-ethanesulfonyl-hex-5-ene-2,3,4-triol).

Comparative Example 3(Perbenzoic Acid Method)

12 l of 1,4-dioxane was added to 1260 g REM and warmed to 40° C., and after determining a dissolution of REM the reaction solution was water-cooled, 5,700 g of metachloro perbenzoic acid (with 68% content) was added gradually to the reaction solution over 4 hours period of time. Then, 12 l ethyl acetate was added to the reaction solution and after leaving to stand overnight the reaction solution was stored in a cold room for 4 hours, and subsequently the deposited crystals were separated out by filtration. A similar operation was repeated using 1,390 g of REM, and the deposited crystals of the first and second operations were mixed together and washed with 15 l of ethyl acetate in a suction funnel. The resultant crystals were air dried over 3 days to obtain 2,965 g of the compound (2) (1,1-bis-ethanesulfonyl-hexane-2,3,4,5-tetraol). An infrared (IR) analysis of the resultant compound (2) revealed an inclusion of metachlorobenzoic aid.

As is clearly understood when comparing the examples 1 through 4 of the present invention with the comparative examples 1 through 3 above, since the method according to the present invention hardly undergoes occurrence of any side reactions, not only the control of reaction time and conditions can be facilitated and the postprocessings may be accomplished with a simplified operation, but also the reaction time can be shortened and a very high yield is achieved.

The invention claimed is:

1. A process for producing a 1,1-bis-alkylsulfonyl compound represented by the general formula (2)

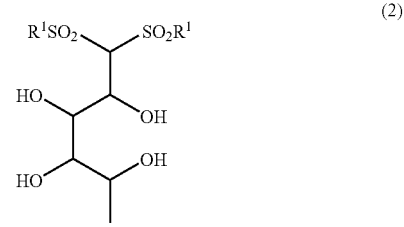

(wherein $R^1$ represents an alkyl group),
comprising:
reacting a 1,1-bis-alkylsulfanyl compound represented by the general formula (1)

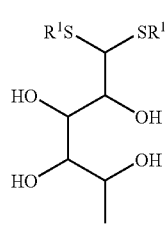
(1)

(wherein, $R^1$ is the same as defined above)
with a monopersulfate.

2. A process for producing an aldehyde compound represented by the general formula (3)

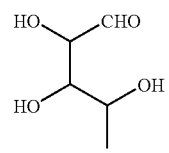
(3)

comprising:
reacting a 1,1-bis-alkylsulfanyl compound represented by the general formula (1)

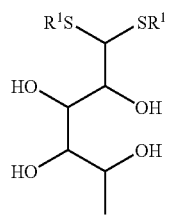
(1)

(wherein $R^1$ represents an alkyl group)
with a monopersulfate to produce a 1,1-bis-alkylsulfonyl compound represented by the general formula (2)

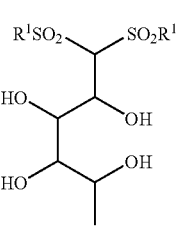
(2)

(wherein, $R^1$ is the same as defined above);
and reacting the resultant 1,1-bis-alkylsulfonyl compound (2) with ammonia.

3. A process for producing a hydrazone derivative represented by the general formula (5)

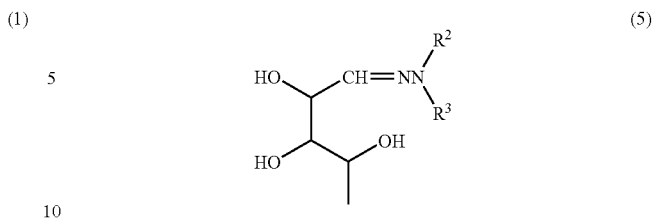
(5)

(wherein $R^2$ and $R^3$, which may be the same or different from each other represent an hydrogen atom, an alkyl group, or an aryl group), comprising:
reacting a 1,1-bis-alkylsulfanyl compound represented by the general formula (1)

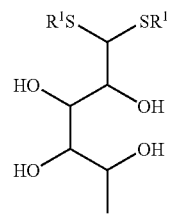
(1)

(wherein $R^1$ represents an alkyl group)
with a monopersulfate to produce a 1,1-bis-alkylsulfonyl compound represented by the general formula (2)

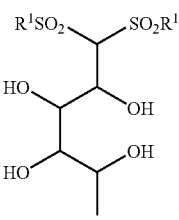
(2)

(wherein $R^1$ is the same as defined above)
and reacting the resultant 1,1-bis-alkylsulfonyl compound (2) with ammonia to produce an aldehyde compound represented by the general formula (3)

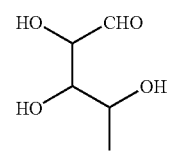
(3)

and reacting with the resultant aldehyde compound (3) with a hydrazine compound represented by the formula (4)

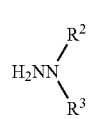
(4)

(wherein $R^2$ and $R^3$ are the same as defined above).

4. A process according to any one of the preceding claims 1 through 3, wherein any reactions thereof are carried out in a water-based solvent or alcohol solvent.

* * * * *